United States Patent
Oishi et al.

(10) Patent No.: US 7,269,993 B2
(45) Date of Patent: Sep. 18, 2007

(54) GAS DETECTING APPARATUS, GAS DETECTING METHOD AND FUEL CELL VEHICLE

(75) Inventors: Hidetoshi Oishi, Utsunomiya (JP); Takashi Sasaki, Shioya-gun (JP); Takashi Saito, Shioya-gun (JP); Hirotoshi Inoue, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 210 days.

(21) Appl. No.: 11/165,714

(22) Filed: Jun. 23, 2005

(65) Prior Publication Data

US 2005/0284208 A1    Dec. 29, 2005

(30) Foreign Application Priority Data

Jun. 29, 2004  (JP)  ............... P 2004-191235
Jun. 29, 2004  (JP)  ............... P 2004-191236
Mar. 9, 2005   (JP)  ............... P 2005-066184

(51) Int. Cl.
*G01N 7/00*  (2006.01)
(52) U.S. Cl. ..................................... 73/23.31
(58) Field of Classification Search ........... 73/23.2, 73/23.31
See application file for complete search history.

(56) References Cited

U.S. PATENT DOCUMENTS

| | | | | |
|---|---|---|---|---|
| 4,298,574 A | * | 11/1981 | Bohl | 422/97 |
| 4,304,204 A | * | 12/1981 | Glockler et al. | 123/691 |
| 4,462,378 A | * | 7/1984 | Atago et al. | 123/568.27 |
| 4,533,520 A | * | 8/1985 | Bossart et al. | 422/96 |
| 4,565,086 A | * | 1/1986 | Orr, Jr. | 73/19.09 |
| 5,025,653 A | * | 6/1991 | Schuldt | 73/23.2 |
| 5,223,783 A | * | 6/1993 | Wilis | 324/71.5 |
| 5,282,383 A | * | 2/1994 | Kayanuma | 73/118.1 |
| 6,308,572 B1 | * | 10/2001 | Ishikawa et al. | 73/597 |
| 6,374,818 B2 | * | 4/2002 | Shinjyo et al. | 123/688 |
| 6,789,533 B1 | * | 9/2004 | Hashimoto et al. | 123/672 |
| 6,842,705 B2 | * | 1/2005 | Moriyama | 702/45 |
| 6,880,329 B2 | * | 4/2005 | Iida et al. | 60/285 |
| 6,888,467 B2 | * | 5/2005 | Green et al. | 340/632 |
| 6,904,355 B2 | * | 6/2005 | Yasui et al. | 701/108 |
| 2003/0061860 A1 | * | 4/2003 | Hu et al. | 73/23.31 |
| 2006/0254340 A1 | * | 11/2006 | Baraket et al. | 73/24.01 |

FOREIGN PATENT DOCUMENTS

| | | | |
|---|---|---|---|
| DE | 608840 A | * | 1/1994 |
| JP | 07-174725 | | 7/1995 |
| JP | 08-075692 | | 3/1996 |
| JP | 2000-221152 | | 8/2000 |

* cited by examiner

*Primary Examiner*—Hezron Williams
*Assistant Examiner*—John Fitzgerald
(74) *Attorney, Agent, or Firm*—Fish & Richardson P.C.

(57) ABSTRACT

The gas detecting system of the present invention is equipped with a catalytic combustion type gas sensor 1a and a semiconductor type gas sensor 1b, in a gas detecting system 1 having an operating sate in which generation of electricity is performed, and an idling state, at the time of the operating state, detection of the detection target gas is performed by the catalytic combustion type gas sensor 1a, whereas at the time of the idling state, detection of the detection target gas is performed by the semiconductor type gas sensor 1b.

7 Claims, 8 Drawing Sheets

GAS DETECTING APPARATUS, GAS DETECTING METHOD AND FUEL CELL VEHICLE

BACKGROUND OF THE INVENTION

1. Field of the Invention

The present invention relates to a gas detecting apparatus, a gas detecting method and a fuel cell vehicle equipped with the gas detecting apparatus.

Moreover, the present invention relates to a gas detecting apparatus equipped with at least two gas sensors each of which concentration outputting characteristic differ.

Priority is claimed on Japanese Patent Application No. 2004-191235, filed Jun. 29, 2004, Japanese-Patent-Application No. 2004-191236, filed Jun. 29, 2004, and Japanese Patent Application No. 2005-066184, filed Mar. 9, 2005, the content of which are incorporated herein by reference.

2. Description of Related Art

Hitherto, for example, in a fuel cell such as a conventional solid polymer membrane type fuel cell, a protecting apparatus having a hydrogen detector (gas sensor) disposed to a discharging system at an oxygen electrode side of the fuel cell is known well. This protecting apparatus cuts supply of fuel when the hydrogen detector (gas sensor) detects that the hydrogen at a fuel side leaks to the oxygen side through a solid polymer electrolyte membrane.

Moreover, as a gas sensor, for example, a gas catalytic combustion type gas sensor is known well. This gas catalytic combustion type gas sensor is equipped with a pair of a gas detecting element which is made from a catalyst such as a platinum and a temperature compensating element, and detects concentration of hydrogen, based on, for example, difference of electrical resistance between the gas detecting element and the temperature compensating element which is at a relatively low temperature such as an ambient temperature, when the gas detecting element becomes a relatively high temperature by heat which generates from combustion when hydrogen comes into contact with a catalyst such as platinum.

For example, the patent document 1 (Japanese Unexamined Patent Application, First Publication No. 2000-221152) has disclosed a technology of reducing power consumption, by turning on electricity intermittently to a heater-cum-an electrode which functions partly as a heater for heating the gas detecting element and partly as an electrode, as this kind of a gas sensor.

However, in the conventional technology, although it is effective for reducing the power consumption of the gas sensor itself, there is a problem of being hard to use it when it is installed into a system which has both an operating state and an idling state, for example, as a fuel cell vehicle, such that the gas detecting operation is kept in the idling state. That is, in the gas sensor of a catalytic combustion type, since the gas detecting element and the temperature compensating element are constituted as a pair of bridge circuits, a circuit which amplifies the output of the element is required, and hence power consumption will increase. Therefore, there is a problem of being hard to use it, because the power is dependent upon the electric power of the power unit which is installed in the system when the system is an idling state.

In particular, in a fuel cell vehicle which uses a fuel cell as a power source, since the battery of which capacity is restricted in the idling state of the vehicle must supply power to the gas sensor, the above-mentioned problem becomes still more significant.

Therefore, it is an object of the present invention to provide a gas detecting system and a fuel cell vehicle which can increase convenience and can perform detection of gas suitable for the state of the system, in a system which has both operating state and an idling state.

Next, in recent years, various sensors are proposed as a gas sensor which detects a detection target gas.

For example, the patent document 2 (Japanese Unexamined Patent Application, First Publication No. H08-75692) has disclosed a technology about a catalytic combustion type gas sensor which uses the combustion heat of the detection target gas (in this case, carbon monoxide gas).

Moreover, the patent document 3 (Japanese Patent No. 3146111) has disclosed a technology about a heat rays type semiconductor type gas sensor having low heat capacity which is equipped with an oxide semiconductor which mainly consists of tin oxide.

However, in the conventional technology, as a sensor to be installed in a system, a sensor of the same type is used. Therefore, detection accuracy will be limited by the peculiar concentration outputting characteristic of the sensor. Therefore, there is a problem that there is a possibility that sufficient detection accuracy cannot be acquired depending on the detection target region.

Therefore, it is another object of the present invention to provide a gas detecting apparatus which can detect concentration of the detection target gas with high accuracy corresponding to the detection target region.

SUMMARY OF THE INVENTION

The first aspect of the present invention is a gas detecting apparatus including at least two gas sensors (for example, the catalytic combustion type gas sensor 1a, the semiconductor type gas sensors 1b and 1b' in the preferred embodiment of the present invention) each of which concentration outputting characteristic differs, in which the gas sensor to be used is switched according to the detection target region, thereby detecting concentration of a detection target gas.

According to the present invention, by using the gas sensor of which output characteristic differs depending on gas concentration, the gas sensor which is more accurate can be used corresponding to the detection target region, and as a result, it is possible to increase detection accuracy of the detection target gas over whole detection target region. Here, the detection target region is the concentration range of the target detection target gas in the system where the above gas detecting apparatus is used, and hence it differs corresponding to the state of the system. That is, a low concentration region of the target detection target gas may become the detection target region, whereas a high concentration region of the target detection target gas may become the detection target region.

The second aspect of the present invention is a gas detecting apparatus as set forth in the first aspect of the present invention, in which the at least two gas sensors are semiconductor type gas sensors each of which concentration outputting characteristic differs.

According to the present invention, by using a semiconductor gas sensor as the at least two gas sensors, it becomes possible to extend lifetime of the gas detecting apparatus, and since a semiconductor type gas sensor has narrow concentration region of gas which is detectable, compared to the other gas sensors, it can increase detection accuracy still higher over whole detection target region by using the semiconductor type gas sensors each of which concentration output characteristic differs.

The third aspect of the present invention is a gas detecting apparatus as set forth in the first aspect of the present invention, in which the gas sensors are a catalytic combustion type gas sensor and a semiconductor type gas sensor, wherein the semiconductor type gas sensor is used for detecting concentration of a detection target gas at the time of changing rate of concentration outputting characteristic of the catalytic combustion gas sensor is less than changing rate of concentration outputting characteristic of the semiconductor type gas sensor, whereas the catalytic combustion type gas sensor is used for detecting concentration of a detection target gas at the time of changing rate of concentration outputting characteristic of the catalytic combustion gas sensor is not less than changing rate of concentration outputting characteristic of the semiconductor type gas sensor.

According to the present invention, by using a semiconductor type gas sensor having a large sensor output at the time of low gas concentration, and a catalytic combustion type gas sensor having a large sensor output at the time of high gas concentration, it is possible to detect concentration of the detection target gas with high accuracy over whole region, without increasing the number of gas detecting element very much. Moreover, in the place where a gas sensor is usually used, when the gas sensor indicates a high gas concentration it is abnormal condition, and hence it is possible to detect gas concentration under normal condition using only the semiconductor type gas sensor which has lifetime being longer compared to the other sensors, and as a result, it is possible to extend the lifetime of the whole of the gas detecting apparatus.

The fourth aspect of the present invention is a gas detecting apparatus as set forth in the third aspect of the present invention, in which the catalytic combustion type gas sensor is used for detecting concentration of a detection target gas until the semiconductor type gas sensor starts detection of gas.

According to the present invention, at the time of starting of gas detection, the catalytic combustion type gas sensor can start up faster than the semiconductor type gas sensor, and hence by performing gas detection using the catalytic combustion type gas sensor until the semiconductor type gas sensor starts detection of gas, it becomes possible to perform detection of concentration of the detection target gas from immediately after starting of the gas sensor, thereby increasing reliability of the gas sensor.

The fifth aspect of the present invention is a gas detecting apparatus as set forth in the first aspect of the present invention, in which the gas sensors are a catalytic combustion type gas sensor (for example, catalytic combustion type gas sensor 1a in the embodiment) and a semiconductor type gas sensor (for example, catalytic combustion type gas sensor 1b in the embodiment), wherein in a gas detecting system having both an operating state in which generating electricity is performed and an idling state, in the operating state the catalytic combustion type gas sensor is used for detecting concentration of a detection target gas, whereas in the idling state the semiconductor type gas sensor is used for detecting concentration of the detection target gas.

According to the present invention, in the operating state, by detecting the detection target gas using the above catalytic combustion type gas sensor, it is possible to make the best use of the characteristic of the catalytic combustion type gas sensor that the output to the detection target gas becomes linear (the shape of a straight line). Therefore, in the operating state, it is possible to detect the detection target gas with a stable accuracy over from high concentration region to low concentration. Moreover, since generation of electricity is performed in the operating state, it is possible to supply electric power stably to the catalytic combustion type gas sensor.

On the other hand, in the idling state, by detecting the detection target gas using the semiconductor type gas sensor, since it is possible to perform detection, while suppressing power consumption, compared to the catalytic combustion type gas sensor, the electric power required to the power supply for operating the semiconductor type gas sensor in the idling state can be reduced, compared to the case of the catalytic combustion type gas sensor. Therefore, it is possible to suppress enlarging the power supply and increasing of cost for the system, thereby increasing the convenience.

Moreover, in the idling state, the source of supply of the detection target gas is stopped and the detection accuracy at a comparatively low concentration region is required, and as a result, it is possible to make the best use of the characteristic of the semiconductor type gas sensor that the output to the concentration of the detection target gas at the low concentration region is high. Therefore, it is possible to perform gas detection suitable for the state of the system.

The sixth aspect of the present invention is a fuel cell vehicle (for example, a fuel-cell vehicle 10) including: a fuel cell which generates electricity by chemical reaction formed by supplying hydrogen gas containing gas and oxygen containing gas, and a gas detecting device as set forth in the first aspect of the present invention, in which the gas sensors are a catalytic combustion type gas sensor and a semiconductor type gas sensor, in an operating state of the fuel cell, the catalytic combustion type gas sensor is used for detecting a detection target gas, whereas in an idling state of the fuel cell, the semiconductor type gas sensor is used for detecting the detection target gas.

According to the present invention, in the operating state, it is possible to detect the detection target gas with a stable accuracy from the high concentration region to the low concentration region, and as a result, it is possible to supply the electric power generated in the fuel cell to the catalytic combustion type gas sensor stably.

On the other hand, in the idling state, the electric power required to the battery for operating the semiconductor type gas sensor can be reduced, compared to the case of the catalytic combustion type gas sensor. Therefore, enlarging the battery mounted in the vehicle and increasing of cost can be suppressed, thereby convenience can be increased, and gas detection suitable for the state of the vehicle can be performed.

The seventh aspect of the present invention is a process for detecting gas including: using at least two gas sensors each of which concentration outputting characteristic differs, wherein the gas sensor to be used is switched according to the detection target region, thereby detecting concentration of a detection target gas.

The eighth aspect of the present invention is a process for detecting gas as set forth in the seventh aspect of the present invention, in which the at least two gas sensors are semiconductor type gas sensors with which concentration outputting characteristic differs.

The ninth aspect of the present invention is a process for detecting gas as set forth in the seventh aspect of the present invention, in which the gas sensors are a catalytic combustion type gas sensor and a semiconductor type gas sensor, wherein the semiconductor type gas sensor is used for detecting concentration of a detection target gas at the time of changing rate of concentration outputting characteristic of the catalytic combustion gas sensor is less than the changing rate of concentration outputting characteristic of the semiconductor type gas sensor, whereas the catalytic combustion type gas sensor is used for detecting concentration of a detection target gas at the time of the changing rate of concentration outputting characteristic of the catalytic combustion gas sensor is not less than changing rate of concentration outputting characteristic of the semiconductor type gas sensor.

The tenth aspect of the present invention is a process for detecting gas as set forth in the seventh aspect of the present invention, in which the catalytic combustion type gas sensor is used for detecting concentration of a detection target gas until the semiconductor type gas sensor starts detection of gas.

The eleventh aspect of the present invention is a process for detecting gas as set forth in the seventh aspect of the present invention, in which the gas sensors are a catalytic combustion type gas sensor and a semiconductor type gas sensor, wherein in a gas detecting system having both an operating state in which generating electricity is performed and an idling state, in the operating state the catalytic combustion type gas sensor is used for detecting concentration of a detection target gas, whereas in the idling state the semiconductor type gas sensor is used for detecting concentration of the detection target gas.

DETAILED DESCRIPTION OF THE INVENTION

Hereinafter, a fuel cell vehicle in the first preferred embodiment of the present invention (it will be referred to as simply "embodiment" below) will be explained with referring to drawings.

Figure 1:
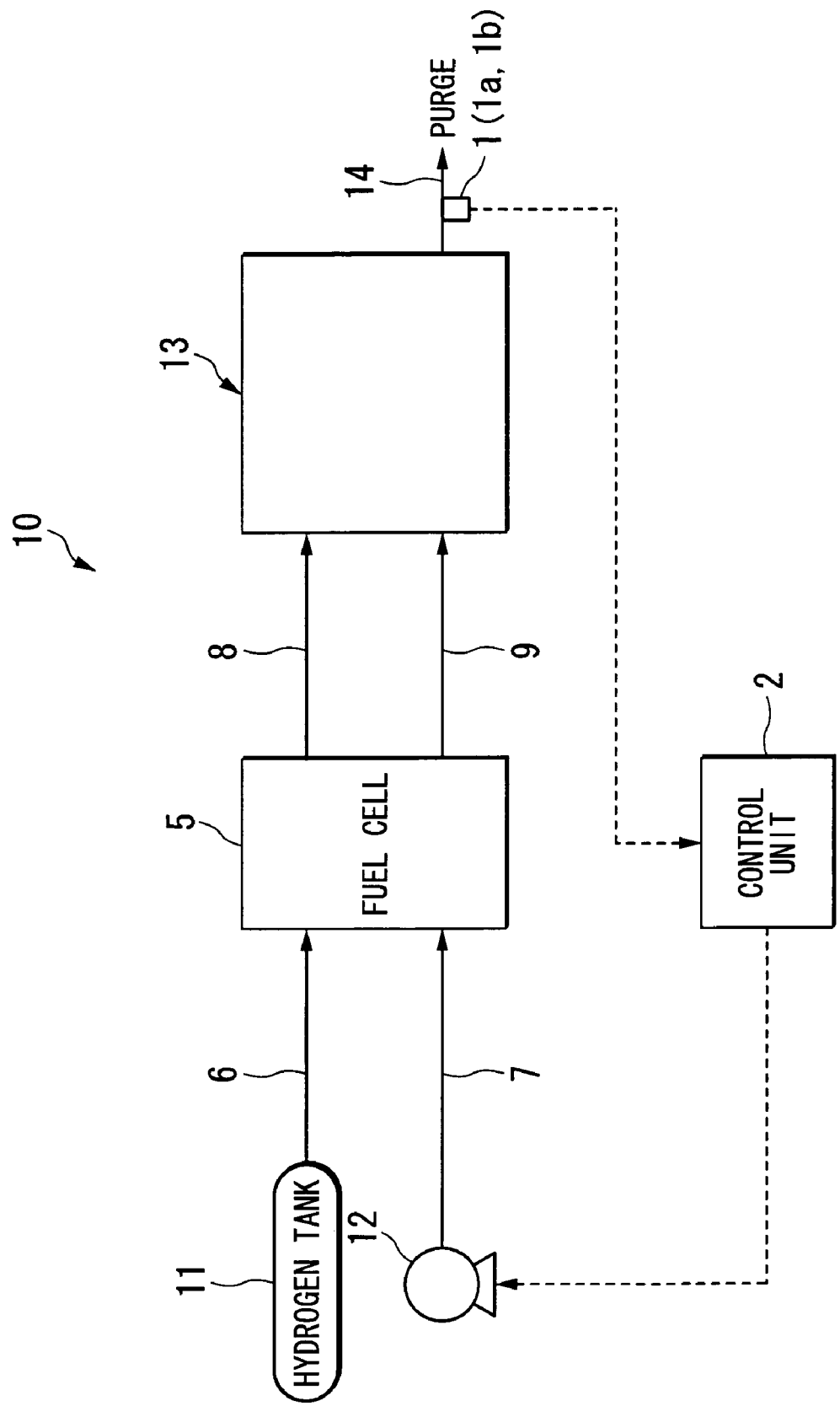
FIG. 1 is a whole block diagram of a fuel cell vehicle in the embodiment of the present invention.

FIG. 1 is an outline block diagram of the fuel cell vehicle in the embodiment.

A fuel cell 5 consists of a stack constituted by laminating plural cells each of which is formed by putting a solid polymer electrolyte membrane which consists of a solid polymer-ion exchange membrane etc., between an anode and a cathode. If hydrogen is supplied to the anode as fuel whereas air which contains oxygen is supplied to the cathode as an oxidizer, then hydrogen ion generated by catalytic reaction at the anode passes through the solid polymer electrolyte membrane to displace to the cathode, thereby performing electrochemical reaction with oxygen at the cathode to generate electricity, and as a result, water is generated.

A part of water generated at the cathode side performs back diffusion to the anode side through the solid polymer electrolyte membrane, and hence generation water also exists also at the anode side.

Air is pressurized to be a predetermined pressure by a compressor 12, and is supplied to the cathode of the fuel cell 5 through an air supply channel 7. The air supplied to the fuel cell 5 is subjected to power generation, and thereafter, it is discharged to the air discharge channel 9 with the generated water at the cathode side from the fuel cell 5, and is introduced into a purge hydrogen dilution apparatus 13.

On the other hand, the hydrogen supplied from a hydrogen tank 11 is supplied to the anode of the fuel cell 5 through a hydrogen supply channel 6. And the hydrogen discharged from the fuel cell 5 is discharged to a hydrogen discharge channel 8. The hydrogen discharge channel 8 is connected to the purge hydrogen dilution apparatus 13.

The hydrogen discharged from the fuel cell 5 is introduced into the purge hydrogen dilution apparatus 13 through the hydrogen discharge channel 8. And hydrogen is diluted by the air introduced into the purge hydrogen dilution apparatus 13 through the air discharge channel 9, and the diluted hydrogen is discharged as emission gas from an exhaust pipe 14.

Figure 2:
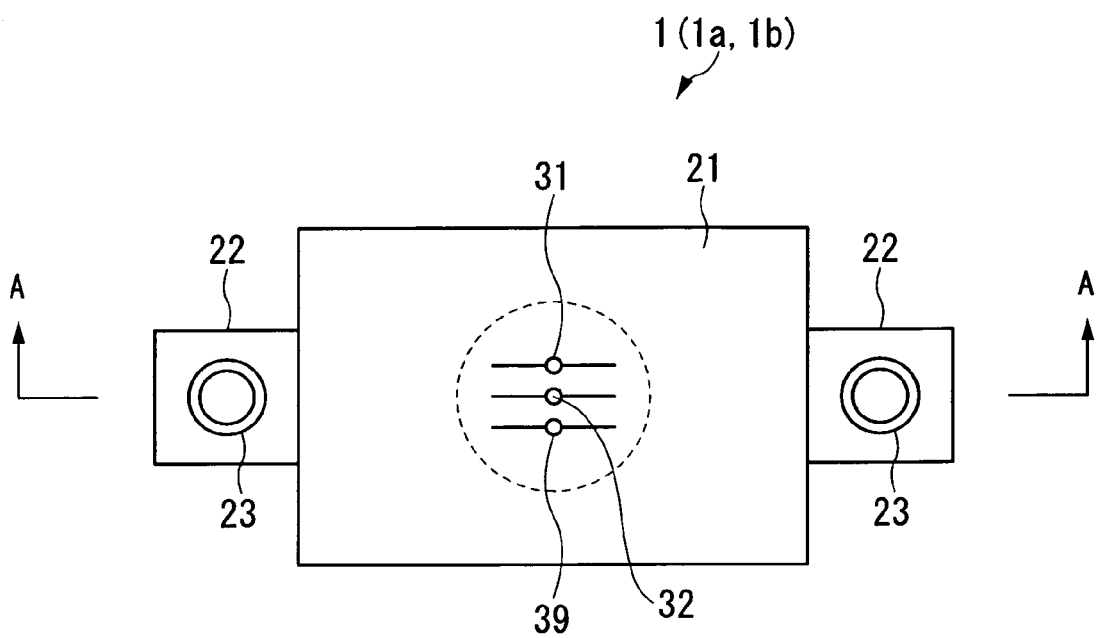
FIG. 2 is a sectional view of the gas sensor shown in FIG. 1.

FIG. 2 is a principal part sectional view of the gas detecting apparatus in the embodiment. As shown in this figure, the gas sensor 1 is disposed to the exhaust pipe 14. The gas sensor 1 is for detecting the hydrogen concentration of the emission gas which circulates the exhaust pipe 14, and the output signal of this gas sensor 1 is inputted into a control unit 2.

The control unit 2 judges whether the abnormal condition of the fuel cell 5 has occurred depending on the comparison result of the detection signal outputted from the gas sensor 1, and a predetermined judgment threshold value, and when it judges with it being an abnormal condition, it outputs an alarm etc., by an alarm device (not shown), for example.

Figure 3:
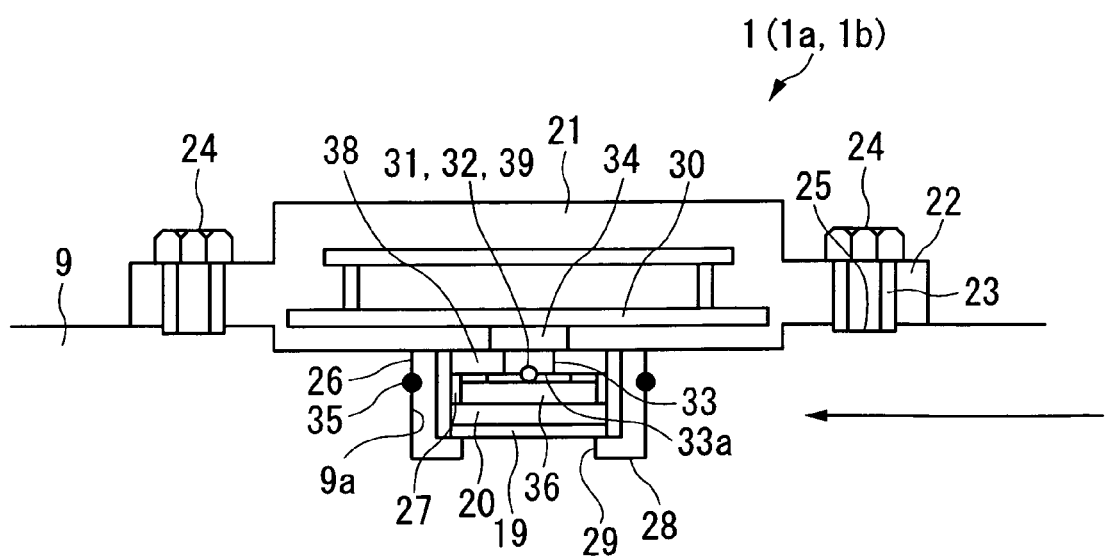
FIG. 3 is an outline sectional view cut along A-A line shown in FIG. 2.

For example, as shown in FIG. 3, the gas sensor 1 is equipped with a case 21 having a shape of a rectangular solid extending in the longitudinal direction of the exhaust pipe 14, i.e., a horizontal direction. The case 21 is made from a polyphenylene sulfide, for example, and is equipped with a flange part 22 on both ends of the longitudinal direction thereof.

Moreover, the cylindrical part 26 is formed on an end surface of the thickness direction of the case 21, the inside of the cylindrical part 26 is formed as a gas detecting part 27, the flange part 28 is formed in the internal side of the gas detecting part 27 toward an inner side, and the inner circumference portion of the flange part 28 constitutes an opening as a gas inlet part 29.

In the case 21, the circuit board 30 sealed by resin is disposed, and a detecting element 31 and a temperature compensating element 32 which are disposed inside the cylindrical part 26 are connected to the circuit board 30. And each of the elements 31 and 32 is disposed to form a pair with intervening a predetermined space therebetween, by plural, for example 4 pieces of stay 33 for turning on electricity and platinum wire 33a which is a lead line being connected to the circuit board 30, at a position apart by a predetermined distance from the base 34 or the metal mother material 38 which are disposed to the bottom side of the gas detecting part 27 in the thickness direction of the gas sensor 1.

Moreover, a seal material 35 is attached to the perimeter surface of the cylindrical part 26, and this seal material 35 is closed to the inner circumference surface of the penetration hole 14a of the exhaust pipe 14, thereby securing airtightness.

The detecting element 31 is an element of a catalytic combustion type, which is constituted by covering the surface of a coil of a metal line which contains platinum having a high temperature coefficient to electric resistance, etc., with a carrier, such as alumina which carries a catalyst consisting of noble metals, etc., which are active to the hydrogen which is the detection target gas.

The temperature compensating element 32 is inactive to the detection target gas, and is, for example, constituted by covering the surface of the same coil as in the detecting element 31 with a carrier, such as alumina.

And it is constituted to cancel the change of electrical resistance due to atmospheric temperature, thereby detecting hydrogen concentration, by using the fact that difference of electrical resistance generates between the detecting element 31 which becomes high temperature by generation of heat of the burning reaction which generates when hydrogen which is the detection target gas comes into contact with the catalyst of the detecting element 31, and the temperature compensating element 32 having a temperature being lower than that of the detecting element 31 because of no generation of burning reaction of the detection target gas.

Moreover, the detecting element 39 is an element of a semiconductor type, which is constituted by putting the sintered compact of the metal oxide semiconductor consisting of tin oxide which is pressed, between a pair of alloy line coil made of platinum type metal, and covering with the same semiconductor material as the circumference of the coil. And hydrogen concentration can be detected by using change of the electric resistance of the semiconductor main body which generates when hydrogen which is the detection target gas comes into contact with the surface of the semiconductor.

Moreover, an approximately rectangle plate heater 36 is disposed to inside the gas detecting part 27. This heater 36 consists of a resistor, etc., and the inside of the gas detecting part 27 and each elements 31, 32, and 39 is heated by turning on electricity to the circuit board 30.

In addition, in the gas detecting part 27, in order to lessen an environmental impact, for example, humidity, and the degree of influence of the detection target gas, a water repellent filter 40 and a filter 41 are disposed.

Thus, the gas sensor 1 in this embodiment is equipped with the catalytic combustion type gas sensor 1a and the semiconductor type gas sensor 1b. The circuit constitution of each sensor 1a and 1b will be explained using FIGS. 5 and 6.

Figure 5:
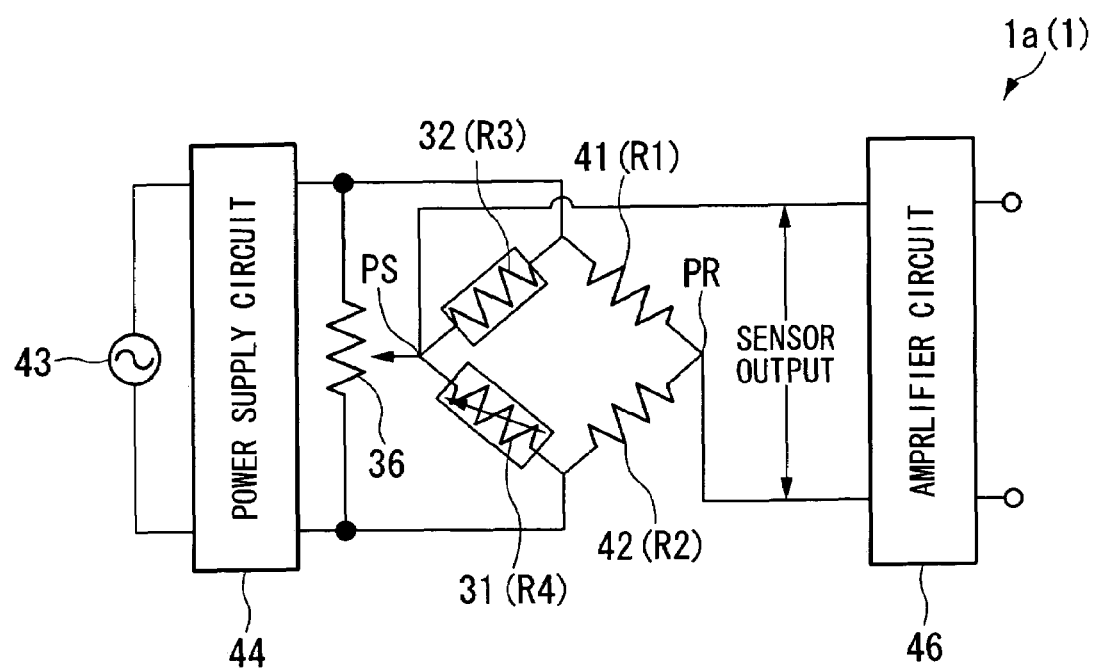
FIG. 5 is a circuit diagram of a catalytic combustion type gas sensor shown in FIG. 1.

As shown in FIG. 5, the catalytic combustion type gas sensor 1a is equipped with a bridge circuit in which a branch constituted by connecting the detecting element 31 (resistance R4) and the temperature compensating element 32 (resistance R3) in series and a branch constituted by connecting a fixed resistance 41 (resistance R1) and a fixed resistance 42 (resistance R2) in series, are connected parallel to a power supply circuit 44. The power supply circuit 44 impresses a predetermined reference voltage based on the voltage supplied from the external power supply 43. The heater 36 is connected to the connecting point PS of the detecting element 31 and the temperature compensating element 32 in the bridge circuit. And between this connecting point PS and the connecting point PR of the fixed resistances 41 and 42, an amplifier circuit 46 which consists of an operational amplifier etc., for example is connected, and it connects with an output circuit (not shown) through this amplifier circuit.

Here, when hydrogen which is the detection target gas does not exist in the gas introduced in the gas detecting part 27, the bridge circuit balances, and is in the state of R1×R4=R2×R3, and the output of the bridge circuit becomes zero. On the other hand, if hydrogen exists, since hydrogen will burn at the catalyst (not shown) of the detecting element 31 to elevate temperature, the resistance R4 will increase. On the other hand, hydrogen does not burn in the temperature compensating element 32, and the resistance R3 will not change. By this, the balance of the bridge circuit breaks, the proper voltage which changes to an increase tendency according to increase change of hydrogen concentration is impressed to the amplifier circuit 46, and the voltage amplified by the amplifier circuit 46 is outputted to the control unit 2. And in the control unit 2, hydrogen concentration is calculated based on the map of the hydrogen concentration beforehand set up according to change of the detection value of this voltage etc.

Figure 6:
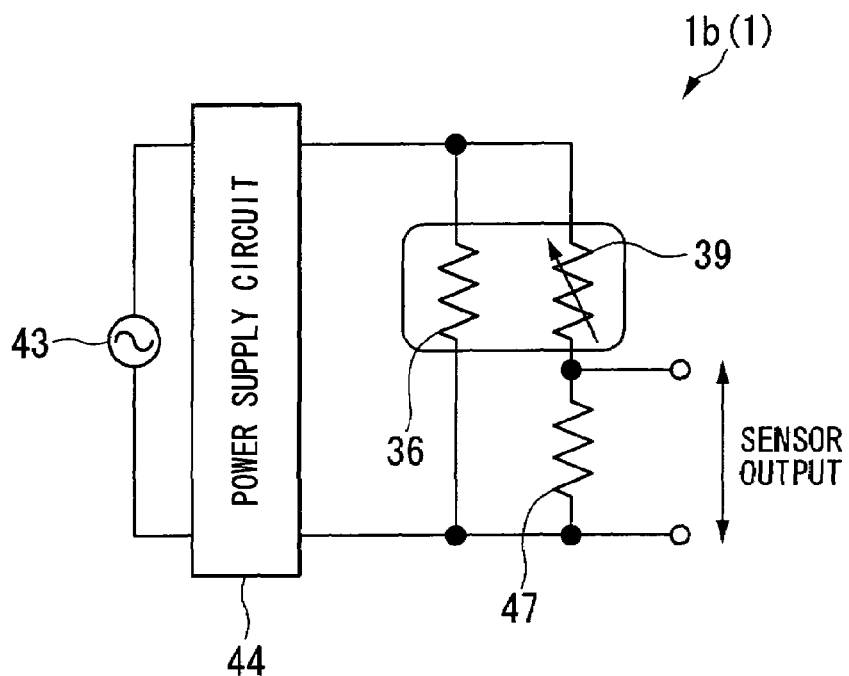
FIG. 6 is a circuit diagram of a semiconductor type gas sensor shown in FIG. 1.

On the other hand, as shown in FIG. 6, in the semiconductor type gas sensor 1b, the detecting element 39 and the heater 36 are connected parallel to the power supply circuit 44, and it is possible to heat the detecting element 39 with the Joule's heat of the heater 36. Moreover, the detecting element 39 is connected to a fixed resistance 47 which is connected to an output circuit (not shown) in series.

Figure 7:
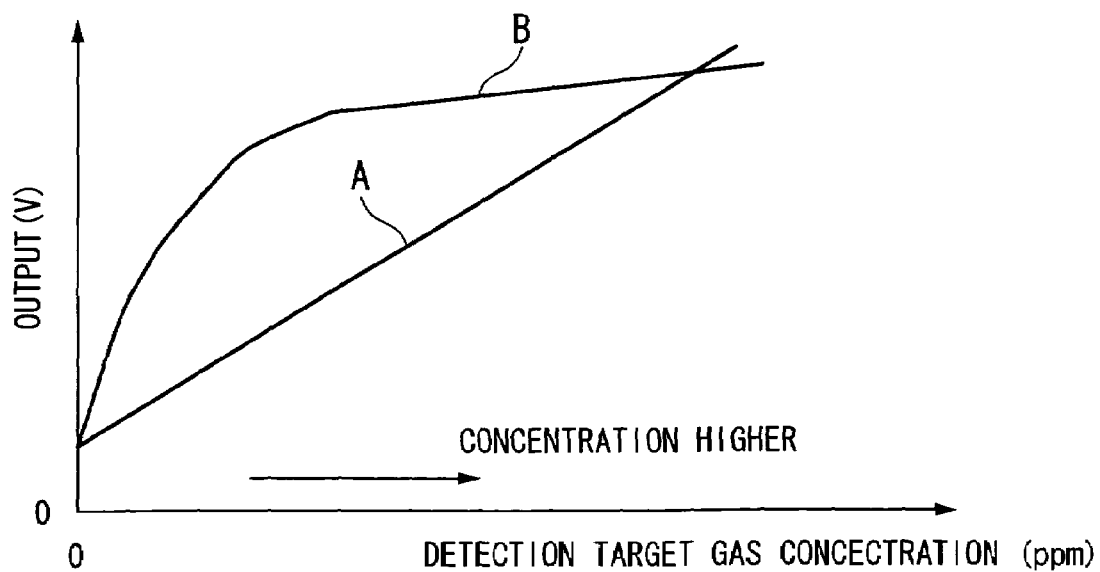
FIG. 7 is a graph showing the correlation between detection target gas concentration and output of a catalytic combustion type gas sensor and a semiconductor type gas sensor.

FIG. 7 is a graph showing the correlation between the concentration of the target gas and the output, in each of the catalytic combustion type gas sensor 1a and the semiconductor type gas sensor 1b.

As shown in this figure, in the catalytic combustion type sensor 1a, the output to the concentration of hydrogen which is the target gas becomes linear (straight line shape), and hence it is possible to perform sensing from a comparatively low concentration region to a high concentration region.

On the other hand, since the semiconductor type gas sensor 1b has the characteristics that the output to the concentration of hydrogen in a low concentration domain is high, and hence it is suitable for sensing at the low concentration region.

In this embodiment, the catalytic combustion type gas sensor 1a detects the detection target gas in the operating state in which generation of electricity is performed by the fuel cell 5. By this, it is possible to make the best use of the characteristic of the catalytic combustion type gas sensor that the output to the concentration of hydrogen which is the detection target gas becomes linear. Therefore, in the operating state, it is possible to detect the detection target gas with a stable accuracy from a high concentration region to a low concentration region. Moreover, since generation of electricity by the fuel cell 5 is performed in the operating state, it is possible to supply electric power stably to the catalytic combustion type gas sensor 1a.

On the other hand, as mentioned above, in the catalytic combustion type gas sensor 1a, hydrogen concentration is detected based on the difference of voltage between the detecting element 31 and the temperature compensating element 32, and hence an amplifier circuit is necessary and as a result the circuit constitution becomes complicated. And as a result, power consumption becomes comparatively large and is not suitable for using it when the vehicle 10 stops.

In this embodiment, the semiconductor type gas sensor 1b detects hydrogen which is the detection target gas in the idling state of the fuel cell vehicle 10. Since the semiconductor type gas sensor 1b reads change of the resistance of the detecting element 39 itself directly, by dividing the loading resistance on the circuit, unlike the catalytic combustion type gas sensor 1a, it can make the amplifier circuit 46 unnecessary. Therefore, it becomes possible to make the circuit constitution simpler, compared to the catalytic combustion type gas sensor 1a, thereby controlling power consumption low.

In this way, it is possible to reduce the electric power required to a power unit (not shown), such as a battery mounted in vehicle 10, in idling state for operating the above semiconductor type gas sensor 1b, compared to the case of the catalytic combustion type gas sensor 1b. Therefore, enlarging of the power unit mounted in vehicle 10 and increasing of cost can be suppressed, thereby increasing the convenience.

Moreover, in the idling state, the supply of hydrogen to the fuel cell 5 is also stopped and the detection accuracy in a comparatively low concentration region is required, and hence it is possible to make the best use of the characteristic of the above semiconductor type gas sensor 1b that the output to the concentration of hydrogen in this low concentration region is high. Therefore, it is possible to perform gas detection suitable for the state of the fuel cell vehicle 10.

Here, the electric power to the sensor 1b in the idling state of the vehicle 10 may be supplied continuously, or intermittently at every predetermined interval.

Figure 4:
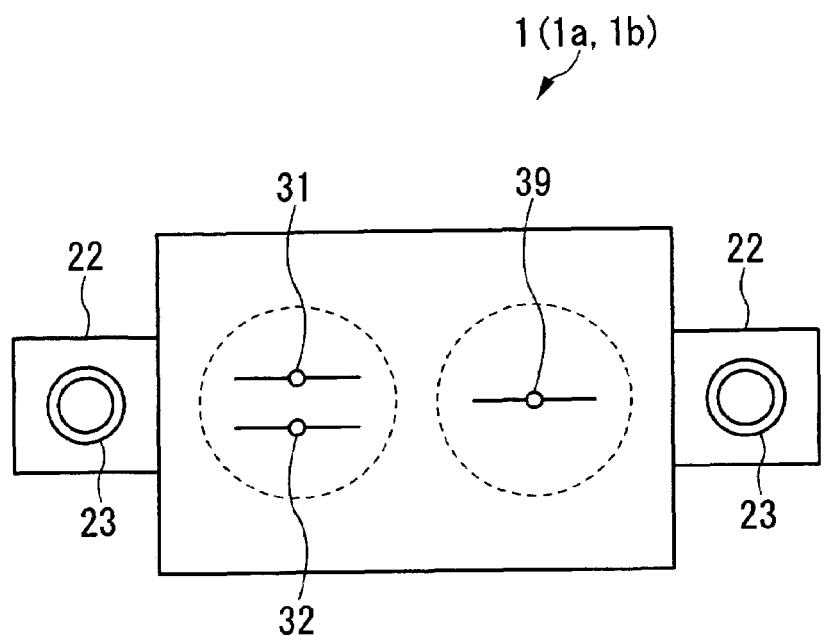
FIG. 4 is a sectional view showing the modified example of the gas sensor shown in FIG. 1.

It should be noted that although a case in which the detecting element 31 of a catalytic combustion type and the detecting element 39 of a semiconductor type are disposed in the same gas detecting part 27 was shown in FIG. 2, it is not restrictive, and it is also possible to dispose the detecting elements 31 and 39 to individual gas detecting parts 27, respectively (refer to FIG. 4).

Moreover, it is of course that the contents of the present invention is not limited to the embodiment. For example, in the embodiment, although the case in which the detection target gas is hydrogen is explained, this is not restrictive, and it is also possible to use the other gas (methanol, the atmospheres, etc.). Moreover, in the embodiment, although the case in which the gas detecting apparatus is applied to the fuel cell system is explained, it is also applicable to the other systems which have operating state and an idling state.

Hereinafter, the gas detecting apparatus in the second preferred embodiment (it will be referred to as simply "embodiment" hereinafter) of the present invention will be explained.

Figure 9:
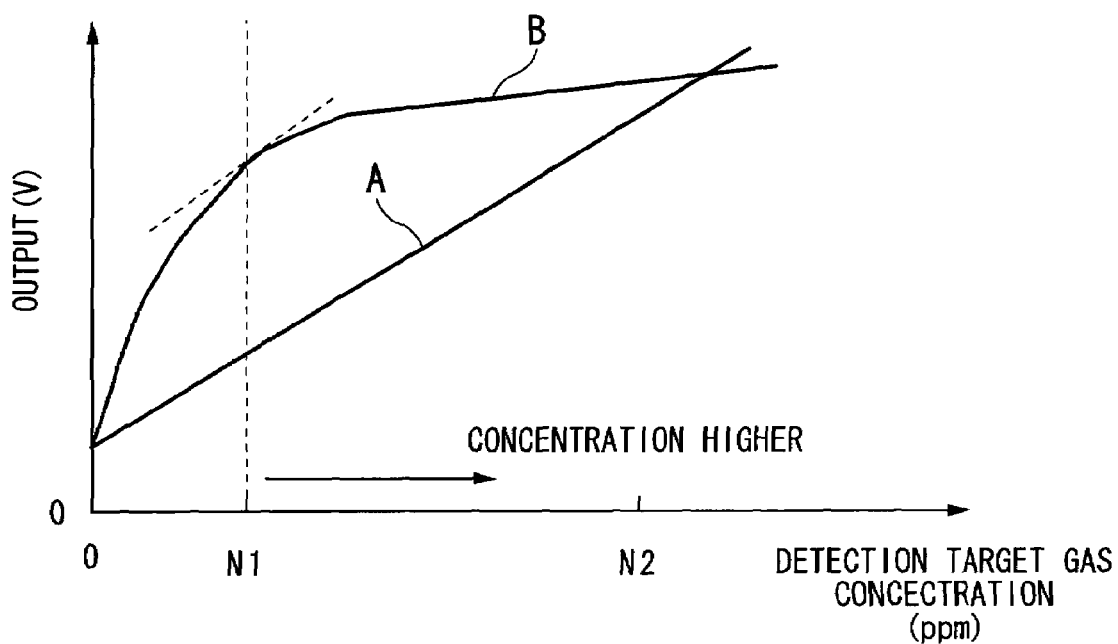
FIG. 9 is a graph showing the correlation between the detection target gas and the output of a catalytic combustion type gas sensor and a semiconductor type gas sensor.

The gas sensor 1 in the form of this embodiment is equipped with a catalytic combustion type gas sensor 1a and a semiconductor type gas sensor 1b. FIG. 9 is a graph showing the correlation between the concentration of the target gas and the output, in each of the catalytic combustion type gas sensor 1a and the semiconductor type gas sensor 1b.

As shown in this figure, in the catalytic combustion type sensor 1a, the output to the concentration of hydrogen which is the target gas becomes linear (straight line shape. Refer to line A), and hence it is possible to perform sensing from a comparatively low concentration region to a high concentration region.

On the other hand, since the semiconductor type gas sensor 1b has the characteristics that the output to the concentration of hydrogen in a low concentration domain is high (Refer to line B), and hence it is suitable for sensing in the low concentration region.

Figure 8:
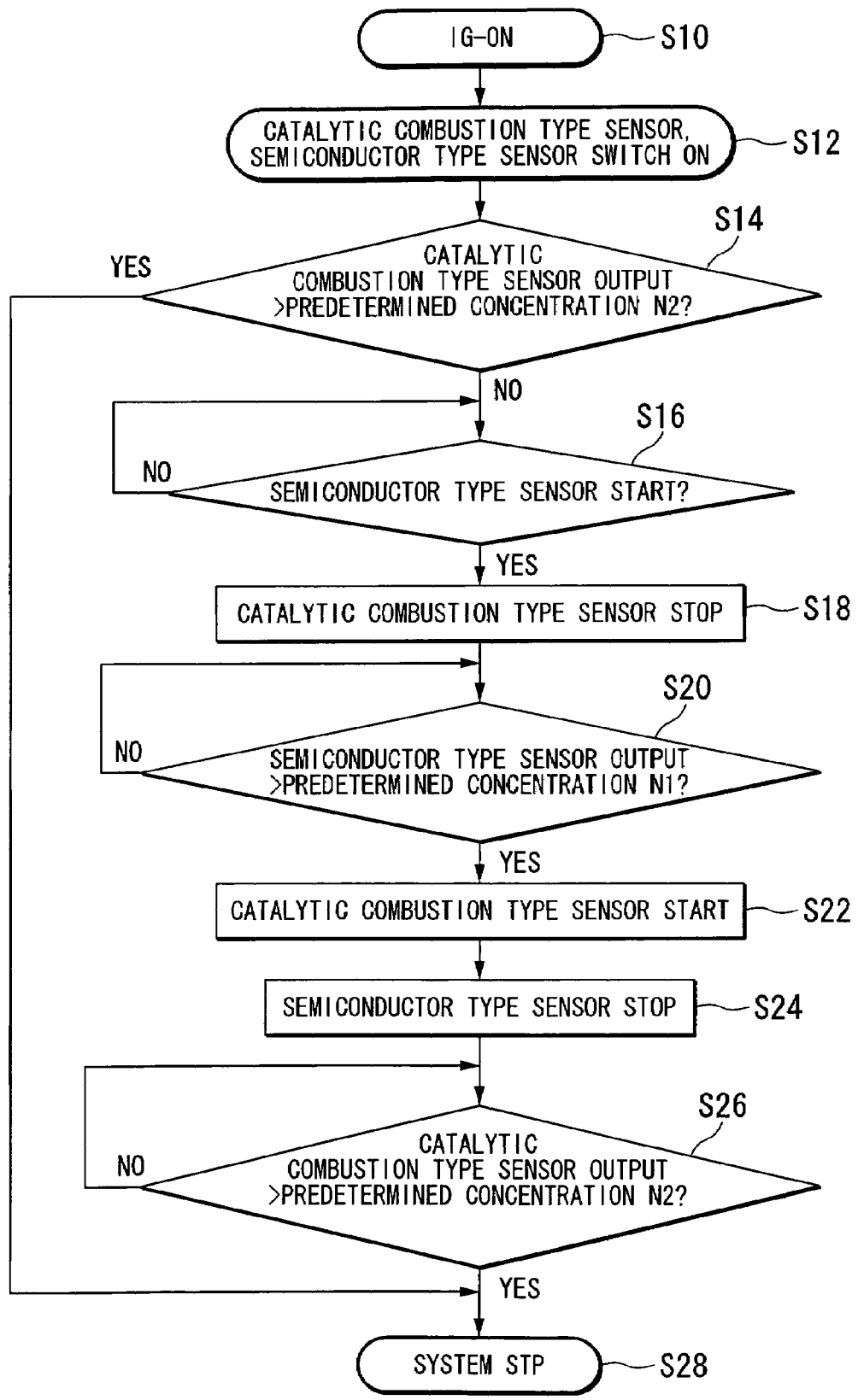
FIG. 8 is a flow chart showing detection processing of the detection target gas using the gas sensor shown in FIG. 1.

The detection processing using the gas sensors 1a and 1b which have such characteristic will be explained using FIG. 8. FIG. 8 is a flow chart showing the detection processing using the gas sensors 1a and 1b shown in FIG. 1. As shown in this figure, at the step S10, an ignition switch is turned ON and operation of the fuel cell vehicle 10 is started. And each switch of the catalytic combustion type gas sensor 1a and the semiconductor type gas sensor 1b is turned ON. Here, by the characteristic of a gas sensor, the catalytic combustion type gas sensor 1a is started earlier than the semiconductor type gas sensor 1b, and will be in the state where the concentration of hydrogen which is the detection target gas is detectable.

In the step S14, it is judged whether the output (detection concentration) in the catalytic combustion type gas sensor 1a is more than a predetermined concentration N2 (refer to FIG. 9). When this judgment result is YES, it progresses to the step S28, the fuel cell vehicle 10 is stopped (system stop), and the reliability of the vehicle 10 is secured.

Moreover, when the judgment result of the step S14 is NO, it progresses to the step S16 and it is judged whether the concentration of hydrogen is detectable or not, that is, whether the semiconductor type gas sensor 1b was started. If this judgment result is YES, it will progress to the step S18 and the catalytic combustion type gas sensor 1a will be stopped. Moreover, if this judgment result is NO, processing of the step S16 will be repeated again.

It progresses to processing of the step S20, after processing the step S18 is completed. In the step S20, it is judged whether the output (detected concentration) of the semiconductor type gas sensor 1b is more than the predetermined concentration N1 or not. Here, the predetermined concentration N1 is the output rate in which out put changing rate of the catalytic combustion type gas sensor 1a will be approximately identical with the output changing rate of the semiconductor type gas sensor 1b. At a concentration larger than this predetermined concentration N1, the output changing rate of the catalytic combustion type gas sensor 1a becomes larger than that of the semiconductor type gas sensor 1b. On the other hand, at a concentration less than the predetermined concentration N1, the output changing rate of the catalytic combustion type gas sensor 1a becomes smaller than that of the semiconductor type gas sensor 1b.

When the judgment result of the step S20 is YES, it progresses to the step S22 to start the catalytic combustion type sensor 1a, and detection by the catalytic combustion type gas sensor 1a is started. Moreover, when the judgment result of the step S20 is NO, detection by the semiconductor type gas sensor 1b is continued, and the step S20 is performed again.

After processing of the step S22, it progresses to the step S24, the semiconductor type gas sensor 1b is stopped, and it shifts to detection by the catalytic combustion type gas sensor 1a. And in the step S26, it judges whether the output (detection concentration) of the catalytic combustion type gas sensor 1a is less than the predetermined concentration N2, and if the judgment result is YES, it will progress to the step S28 to stop the system (the fuel cell vehicle 10). Moreover, if this judgment result is NO, detection by the catalytic combustion type gas sensor 1a will be continued, and the step S26 will be performed again.

In this embodiment, the semiconductor type gas sensor 1b detects the concentration of the detection target gas when the changing rate of the concentration outputting characteristic of the catalytic combustion type gas sensor 1a is less than the changing rate of the concentration outputting characteristic of the semiconductor type gas sensor 1b (at the time of concentration is ranging from 0 to N1). Whereas, when the changing rate of the concentration outputting characteristic of the catalytic combustion type gas sensor 1a is larger than the changing rate of the concentration outputting characteristic of the semiconductor type gas sensor 1b, the catalytic combustion type gas sensor 1a detects the concentration of the detection target gas.

Thus, in this embodiment, at the time of low concentration, the semiconductor type gas sensor 1b having a large sensor output is used, and the concentration of the detection target gas (in this case, hydrogen) can be detected with high accuracy in all regions by using the catalytic combustion type gas sensor 1a having a large sensor output at the time of high concentration, without increasing the number of the gas detecting elements 31, 32, and 39 very much. Moreover, at the place where the gas sensor 1 is usually used, the case of indicating high concentration is abnormal, and hence it is possible to perform gas detection usually using only the semiconductor type gas sensor 1b having a long lifetime compared to the other sensors, and as a result, it is possible to extend the lifetime of whole gas detecting apparatus.

Figure 10:
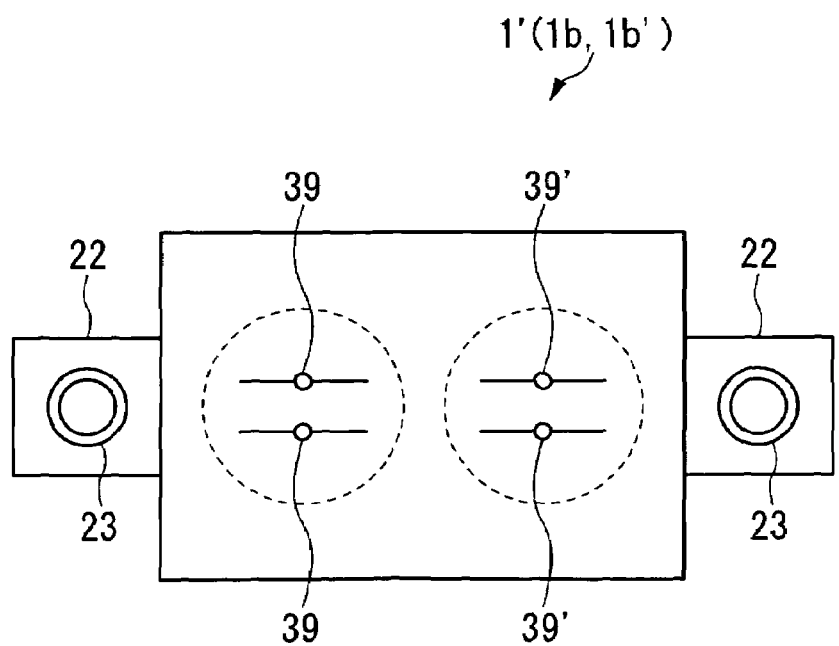
FIG. 10 is a sectional view showing the modified example of the gas sensor shown in FIG. 1.

Moreover, as shown in FIG. 10, it is also possible to constitute the gas sensor 1' from two semiconductor type gas sensors 1b and 1b'. Each of the semiconductor type gas sensors 1b and 1b' has a semiconductor type detecting elements 39 and 39', respectively.

Figure 11:
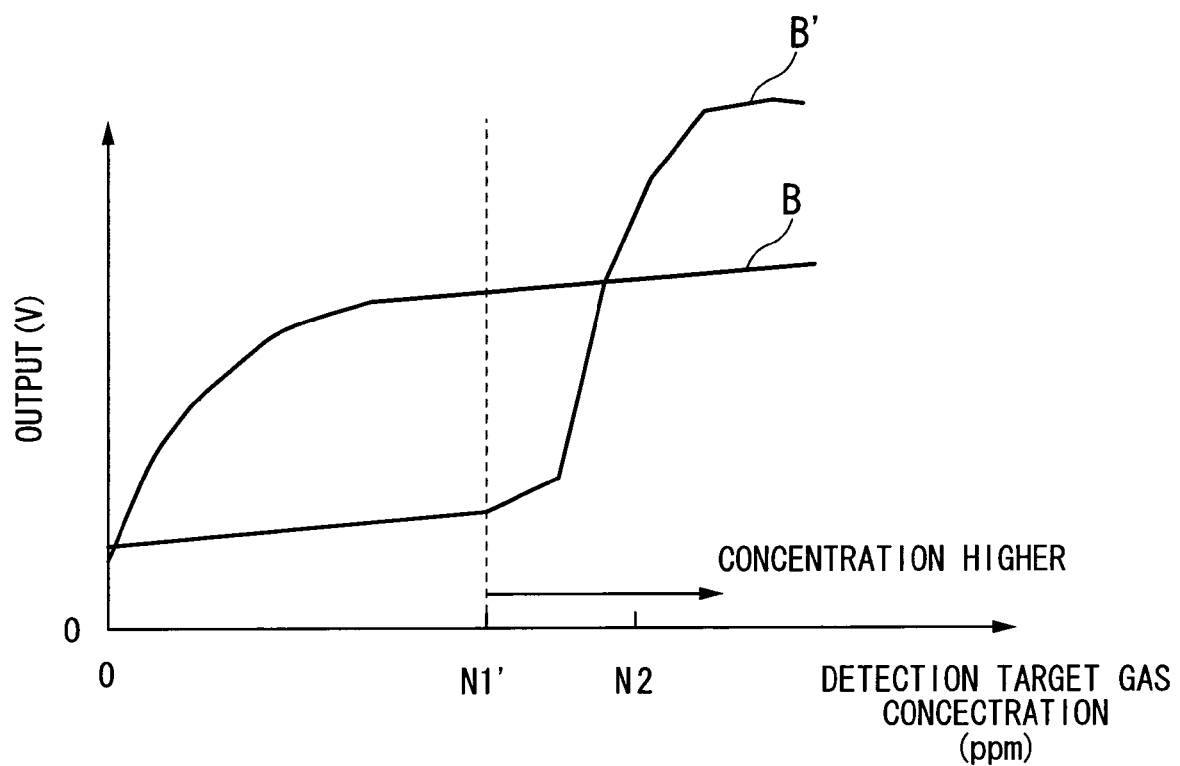
FIG. 11 is a graph showing the correlation between the concentration of detection target gas and output, of a low concentration region semiconductor type gas sensor and a high concentration region semiconductor type gas sensor.

FIG. 11 is a graph showing the correlation between the concentration of the target gas and the output of each semiconductor type gas sensors 1b and 1b'. As shown in this figure, the gas sensor 1b is a low concentration region semiconductor type gas sensor 1b which has a high output characteristic in low concentration (less than the predetermined value N1') (line B), whereas the gas sensor 1b' is a high concentration region semiconductor type gas sensor 1b' which has a high output characteristic in high concentration (not less than the predetermined value N1') (line B').

And when the detection target region is low concentration, detection is performed using the low concentration region semiconductor type gas sensor 1b, whereas when the detection target region is high concentration, detection is performed using the high concentration region semiconductor type gas sensor 1b'. Thus, by using the semiconductor type gas sensors 1b and 1b', it becomes possible to extend lifetime of the gas detecting apparatus. Moreover, the individual detectable gas concentration region of the semiconductor type gas sensors 1b and 1b' is narrow compared to the other gas sensors such as the catalytic combustion type gas sensor 1a, and hence it becomes possible to increase detection accuracy over whole detection target region still further, by using the semiconductor type gas sensors 1b and 1b' having different concentration outputting characteristic.

Hereinafter, the gas detecting apparatus in the third embodiment (it will be referred to as simply "embodiment" hereinafter) of the present invention will be explained.

The gas sensor 1 in this embodiment is equipped with a catalytic combustion type gas sensor 1a and a semiconductor type gas sensor 1b. FIG. 9 is a graph showing the correlation between the concentration of the target gas and the output, in each of the catalytic combustion type gas sensor 1a and the semiconductor type gas sensor 1b.

As shown in this figure, in the catalytic combustion type sensor 1a, the output to the concentration of hydrogen which is the target gas becomes linear (straight line shape. Refer to line A), and hence it is possible to perform sensing from a comparatively low concentration region to a high concentration region.

On the other hand, since the semiconductor type gas sensor 1b has the characteristics that the output to the concentration of hydrogen in a low concentration domain is high (Refer to line B), and hence it is suitable for sensing in the low concentration region.

Figure 12:
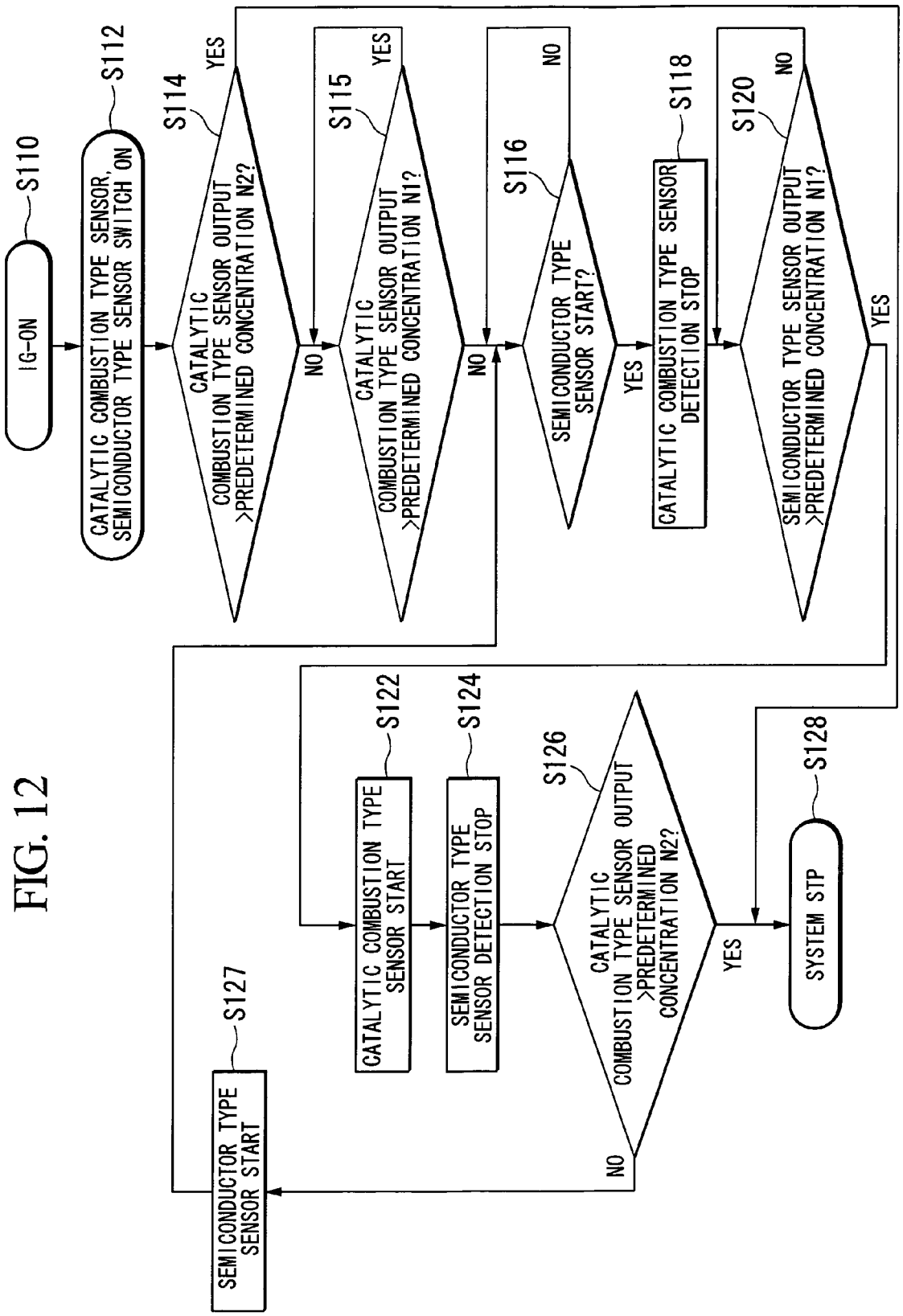
FIG. 12 is a flow chart showing detection processing of the detection target gas using the gas sensor shown in FIG. 1.

The detection processing using the gas sensors 1a and 1b which have such characteristic will be explained using FIG. 12. FIG. 12 is a flow chart showing the detection processing using the gas sensors 1a and 1b shown in FIG. 1. As shown in this figure, at the step S110, an ignition switch is turned ON and operation of the fuel cell vehicle 10 is started. And each switch of the catalytic combustion type gas sensor 1a and the semiconductor type gas sensor 1b is turned ON. Here, by the characteristic of a gas sensor, the catalytic combustion type gas sensor 1a is started earlier than the semiconductor type gas sensor 1b, and will be in the state where the concentration of hydrogen which is the detection target gas is detectable.

In the step S114, it is judged whether the output (detected concentration) in the catalytic combustion type gas sensor 1a is more than a predetermined concentration N2 (refer to FIG. 9). When this judgment result is YES, it progresses to the step S128, the fuel cell vehicle 10 is stopped (system stop), and the reliability of the vehicle 10 is secured.

Moreover, when the judgment result of the step S114 is NO, it progresses to the step S115 and it is judged whether the output (detected concentration) in the catalytic combustion type gas sensor 1a is less than the predetermined concentration N1 or not. Here, the predetermined concentration N1 is the output rate in which output changing rate of the catalytic combustion type gas sensor 1a will be approximately identical with the output changing rate of the semiconductor type gas sensor 1b. At a concentration larger than this predetermined concentration N1, the output changing rate of the catalytic combustion type gas sensor 1a becomes larger than that of the semiconductor type gas sensor 1b. On the other hand, at a concentration smaller than the predetermined concentration N1, the output changing rate of the catalytic combustion type gas sensor 1a becomes smaller than that of the semiconductor type gas sensor 1b.

When this judgment result is YES, processing of the step S115 is repeated, whereas when this judgment result is NO, it progresses to processing of the step S116. Thus, when the output in the catalytic combustion type gas sensor 1a is larger than the predetermined concentration N1, the detection processing using the catalytic combustion type gas sensor 1a which is advantageous on the outputting characteristic is performed continuously.

On the other hand, in the step S116, it is judged whether the semiconductor type gas sensor 1b was started or not, that is, whether the concentration of hydrogen is detectable by the semiconductor type gas sensor 1b or not. If this judgment result is YES, it will progress to the step S118 to stop the catalytic combustion type gas sensor 1a. Moreover, if this judgment result is NO, processing of the step S116 will be repeated again.

It progresses to processing of the step S120, after processing of the step S118 is completed. In the step S20, it is judged whether the output (detected concentration) of the semiconductor type gas sensor 1b is less than the predetermined concentration N1 mentioned above or not.

When the judgment result of the step S120 is YES, it progresses to the step S122 to start the catalytic combustion type sensor 1a, thereby starting detection by the catalytic combustion type gas sensor 1a. Whereas, when the judgment result of the step S120 is NO, detection by the semiconductor type gas sensor 1b is continued, and Step S120 is performed again.

After processing of the step S122, it progresses to the step S124 to stop the semiconductor type gas sensor 1b, and it shifts to detection by the catalytic combustion type gas sensor 1a. And in the step S126, it judges whether the output (detected concentration) of the catalytic combustion type gas sensor 1a is less than the predetermined concentration N2, and if the judgment result is YES, it will progress to the step S128 to stop the system (the fuel cell vehicle 10). Whereas, if this judgment result is NO, it progresses to the step S127, while continuing the detection by the catalytic combustion type gas sensor 1a. In the step S127, the semiconductor type gas sensor 1b is started, and thereafter, processing of the step S116 mentioned above is processed again.

In this embodiment, the semiconductor type gas sensor 1b detects the concentration of the detection target gas when the changing rate of the concentration outputting characteristic of the catalytic combustion type gas sensor 1a is less than the changing rate of the concentration outputting characteristic of the semiconductor type gas sensor 1b (at the time of concentration is ranging from 0 to N1). Whereas, when the changing rate of the concentration outputting characteristic of the catalytic combustion type gas sensor 1a is not less than the changing rate of the concentration outputting characteristic of the semiconductor type gas sensor 1b, the catalytic combustion type gas sensor 1a detects the concentration of the detection target gas.

Thus, in this embodiment, at the time of low concentration, the semiconductor type gas sensor 1b having a large sensor output is used, and the concentration of the detection target gas (in this case, hydrogen) can be detected with high accuracy in all regions by using the catalytic combustion type gas sensor 1a having a large sensor output at the time of high concentration, without increasing the number of the gas detecting elements 31, 32, and 39 very much. Moreover, at the place where the gas sensor 1 is usually used, the case of indicating high concentration is abnormal, and hence it is possible to perform gas detection usually using only the semiconductor type gas sensor 1b having a long lifetime compared to the other sensors, and as a result, it is possible to extend the lifetime of the whole gas detecting apparatus.

According to the first aspect of the present invention, it is possible to increase detection accuracy of the detection target gas over the whole detection target region.

According to the second aspect of the present invention, life time as the gas detecting apparatus can be extended, and detection accuracy can be increased still further over the whole detection target region.

According to the third aspect of the present invention, the concentration of the detection target gas can be detected with high accuracy over whole region, without increasing the number of the gas detecting element very much, and to extend lifetime as the whole gas detecting apparatus.

According to the fourth aspect of the present invention, it becomes possible from immediately after starting of the gas detecting apparatus to perform detection of the concentration of the detection target gas, and to improve reliability of the gas detecting apparatus.

According to the fifth aspect of the present invention, enlarging of a power supply and increasing of cost of the system can be suppressed, thereby improving the convenience. Moreover, detection of gas suitable for the state of a system can be performed.

According to the sixth aspect of the present invention, enlarging of the battery mounted in the vehicle and increasing of cost can be suppressed, thereby improving the convenience. Moreover, detection of gas suitable for the state of the vehicle can be performed.

What is claimed is:

1. A gas detecting apparatus comprising at least two gas sensors each of which concentration outputting characteristic differs, wherein the gas sensor to be used is switched according to the detection target region, thereby detecting concentration of a detection target gas, and
   wherein the gas sensors are a catalytic combustion type gas sensor and a semiconductor type gas sensor, wherein the semiconductor type gas sensor is used for detecting concentration of a detection target gas at the time of changing rate of concentration outputting characteristic of the catalytic combustion gas sensor is less than changing rate of concentration outputting characteristic of the semiconductor type gas sensor, whereas the catalytic combustion type gas sensor is used for detecting concentration of a detection target gas at the time of changing rate of concentration outputting characteristic of the catalytic combustion gas sensor is not less than changing rate of concentration outputting characteristic of the semiconductor type gas sensor.

2. A gas detecting apparatus as set forth in claim 1, wherein the catalytic combustion type gas sensor is used for detecting concentration of a detection target gas until the semiconductor type gas sensor starts detection of gas.

3. A gas detecting apparatus as set forth in claim 1, wherein the gas sensors are a catalytic combustion type gas sensor and a semiconductor type gas sensor, wherein in a gas detecting system having both an operating state in which generating is performed and an idling state, in the operating state the catalytic combustion type gas sensor is used for detecting concentration of a detection target gas, whereas in the idling state the semiconductor type gas sensor is used for detecting concentration of the detection target gas.

4. A fuel cell vehicle comprising: a fuel cell which generates electricity by chemical reaction formed by supplying hydrogen gas containing gas and oxygen containing gas, and a gas detecting device as set forth in claim 3, wherein the gas sensors are a catalytic combustion type gas sensor and a semiconductor type gas sensor, in an operating state of the fuel cell, the catalytic combustion type gas sensor is used for detecting a detection target gas, whereas in an idling state of the fuel cell, the semiconductor type gas sensor is used for detecting the detection target gas.

5. A process for detecting gas comprising: using at least two gas sensors each of which concentration outputting characteristic differs, wherein the gas sensor to be used is switched according to the detection target region, thereby detecting concentration of a detection target gas, and
   wherein the gas sensors are a catalytic combustion type gas sensor and a semiconductor type gas sensor, wherein the semiconductor type gas sensor is used for detecting concentration of a detection target gas at the time of changing rate of concentration outputting characteristic of the catalytic combustion gas sensor is less than changing rate of concentration outputting characteristic of the semiconductor type gas sensor, whereas the catalytic combustion type gas sensor is used for detecting concentration of a detection target gas at the time of changing rate of concentration outputting characteristic of the catalytic combustion gas sensor is not less than changing rate of concentration outputting characteristic of the semiconductor type gas sensor.

6. A process for detecting gas as set forth in claim 5, wherein the catalytic combustion type gas sensor is used for detecting concentration of a detection target gas until the semiconductor type gas sensor starts detection of gas.

7. A process for detecting gas as set forth in claim 5, wherein the gas sensors are a catalytic combustion type gas sensor and a semiconductor type gas sensor, wherein in a gas detecting system having both an operating state in which generating is performed and an idling state, in the operating state the catalytic combustion type gas sensor is used for detecting concentration of a detection target gas, whereas in the idling state the semiconductor type gas sensor is used for detecting concentration of the detection target gas.

* * * * *